(12) United States Patent
Saarikko et al.

(10) Patent No.: US 9,759,913 B2
(45) Date of Patent: *Sep. 12, 2017

(54) EYE TRACKING APPARATUS, METHOD AND SYSTEM

(71) Applicant: Microsoft Technology Licensing, LLC, Redmond, WA (US)

(72) Inventors: Pasi Saarikko, Espoo (FI); Xinye Lou, Kirkland, WA (US); Scott McEldowney, Redmond, WA (US); Steven Robbins, Redmond, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/255,934

(22) Filed: Sep. 2, 2016

(65) Prior Publication Data

US 2016/0370583 A1    Dec. 22, 2016

Related U.S. Application Data

(63) Continuation of application No. 14/140,987, filed on Dec. 26, 2013, now Pat. No. 9,459,451.

(51) Int. Cl.
*G02B 6/34* (2006.01)
*G03H 1/00* (2006.01)
(Continued)

(52) U.S. Cl.
CPC .......... *G02B 27/0093* (2013.01); *A61B 3/113* (2013.01); *G02B 6/02085* (2013.01);
(Continued)

(58) Field of Classification Search
CPC ............ G02B 27/0093; G02B 27/0172; G02B 27/0174; G02B 27/0107; G02B 27/0187;
(Continued)

(56) References Cited

U.S. PATENT DOCUMENTS 3,861,784 A    1/1975  Torok
4,235,504 A    11/1980 Ikeda
(Continued)

FOREIGN PATENT DOCUMENTS

CA    2013163347 A1    9/1984
EP    2290428 A2       2/2011
(Continued)

OTHER PUBLICATIONS

Iwamoto, Kazuyo, et al., "Eye Movement Tracking Type Image Display System for Wide Image Presentation with High-resolution-Evaluation of High-resolution Image Presentation," Proceedings of the 2002 IEEE/RSJ Intl. Conference on Intelligent Robots and Systems EPFL, Oct. 2002, 6 pages.
(Continued)

*Primary Examiner* — Robert Tavlykaev
(74) *Attorney, Agent, or Firm* — Vierra Magen Marcus LLP

(57) ABSTRACT

A transparent waveguide for use in eye tracking includes an input-coupler and an output-coupler. The input-coupler comprises a plurality of curved grating lines having a radially varying pitch. When positioned in front of an eye illuminated with infrared light, infrared light beams reflected from the eye and incident on the input-coupler enter the waveguide at the input-coupler, propagate through the waveguide by way of total internal reflections, and exit the waveguide proximate the output-coupler. The radially varying pitch of the curved grating lines of the input-coupler provides angular encoding of infrared light incident on the input-coupler, and more specifically, causes different beams of infrared light incident on respective different horizontal and vertical positions of the input-coupler to propagate through the waveguide at respective different angles of reflection and exit the waveguide at respective different angles of incidence relative to a surface of the waveguide through which infrared light beams exit.

20 Claims, 9 Drawing Sheets

(51) Int. Cl.
*G09G 5/00* (2006.01)
*G02B 27/00* (2006.01)
*G02B 6/02* (2006.01)
*H04N 13/04* (2006.01)
*G06F 3/01* (2006.01)
*A61B 3/113* (2006.01)
*G02B 27/01* (2006.01)

(52) U.S. Cl.
CPC ............ *G02B 6/34* (2013.01); *G02B 27/0172* (2013.01); *G06F 3/013* (2013.01); *H04N 13/0484* (2013.01); *G02B 2027/0107* (2013.01); *G02B 2027/0138* (2013.01); *G02B 2027/0178* (2013.01)

(58) Field of Classification Search
CPC . G02B 6/02085; H04N 13/0484; A61B 3/113
USPC ....... 385/37; 359/34; 438/E13.045, E13.047; 345/8
See application file for complete search history.

(56) References Cited

U.S. PATENT DOCUMENTS

| | | | |
|---|---|---|---|
| 4,711,512 | A | 12/1987 | Upatnieks |
| 5,383,042 | A | 1/1995 | Robinson |
| 5,440,669 | A | 8/1995 | Rakuljic et al. |
| 5,491,570 | A | 2/1996 | Rakuljic et al. |
| 5,614,988 | A | 3/1997 | Kato et al. |
| 5,701,132 | A | 12/1997 | Kollin et al. |
| 5,856,842 | A | 1/1999 | Tedesco |
| 5,886,822 | A | 3/1999 | Spitzer |
| 5,966,223 | A | 10/1999 | Friesem et al. |
| 5,986,746 | A | 11/1999 | Metz et al. |
| 6,285,813 | B1 | 9/2001 | Schultz et al. |
| 6,323,970 | B1 | 11/2001 | Popovich |
| 6,529,331 | B2 | 3/2003 | Massof |
| 6,580,529 | B1 | 6/2003 | Amitai et al. |
| 6,791,760 | B2 | 9/2004 | Janeczko et al. |
| 6,804,066 | B1 | 10/2004 | Ha et al. |
| 7,184,615 | B2 | 2/2007 | Levola |
| 7,190,859 | B2 | 3/2007 | Greiner et al. |
| 7,205,960 | B2 | 4/2007 | David |
| 7,283,705 | B2 | 10/2007 | Paek et al. |
| 7,401,920 | B1 | 7/2008 | Kranz et al. |
| 7,576,916 | B2 | 8/2009 | Amitai |
| 7,619,739 | B1 | 11/2009 | Sutherland et al. |
| 7,660,047 | B1 | 2/2010 | Travis et al. |
| 7,907,342 | B2 | 3/2011 | Simmonds et al. |
| 8,068,709 | B2 | 11/2011 | Iazikov et al. |
| 8,160,411 | B2 | 4/2012 | Levola et al. |
| 8,233,204 | B1 | 7/2012 | Robbins et al. |
| 8,432,589 | B2 | 4/2013 | Tompkin et al. |
| 8,487,838 | B2 | 7/2013 | Lewis et al. |
| 8,611,014 | B2 | 12/2013 | Valera et al. |
| 8,638,498 | B2 | 1/2014 | Bohn et al. |
| 8,817,350 | B1 | 8/2014 | Robbins et al. |
| 2003/0184868 | A1 | 10/2003 | Geist |
| 2005/0105084 | A1 | 5/2005 | Wang et al. |
| 2006/0132914 | A1 | 6/2006 | Weiss et al. |
| 2007/0041684 | A1 | 2/2007 | Popovich et al. |
| 2008/0129530 | A1 | 6/2008 | Lokos |
| 2009/0128901 | A1 | 5/2009 | Tilleman |
| 2009/0323737 | A1 | 12/2009 | Ensher et al. |
| 2010/0079865 | A1 | 4/2010 | Saarikko et al. |
| 2010/0149073 | A1 | 6/2010 | Chaum et al. |
| 2010/0157400 | A1 | 6/2010 | Dimov et al. |
| 2011/0037951 | A1 | 2/2011 | Hua et al. |
| 2011/0109528 | A1 | 5/2011 | Mun et al. |
| 2011/0122305 | A1 | 5/2011 | Kobayashi |
| 2012/0017153 | A1 | 1/2012 | Matsuda et al. |
| 2012/0038918 | A1 | 2/2012 | Liu et al. |
| 2012/0081769 | A1 | 4/2012 | Dergachev |
| 2012/0120493 | A1 | 5/2012 | Simmonds et al. |
| 2012/0236030 | A1 | 9/2012 | Border |
| 2013/0077049 | A1 | 3/2013 | Bohn |
| 2013/0101253 | A1 | 4/2013 | Popovich et al. |
| 2013/0222384 | A1 | 8/2013 | Futterer |
| 2013/0250431 | A1 | 9/2013 | Robbins et al. |
| 2013/0278631 | A1 | 10/2013 | Border et al. |
| 2013/0286178 | A1 | 10/2013 | Lewis et al. |
| 2013/0300637 | A1 | 11/2013 | Smits et al. |
| 2013/0314793 | A1 | 11/2013 | Robbins et al. |
| 2014/0010265 | A1 | 1/2014 | Peng |
| 2014/0016051 | A1 | 1/2014 | Kroll et al. |
| 2014/0044143 | A1 | 2/2014 | Clarkson et al. |
| 2014/0104665 | A1 | 4/2014 | Popovich et al. |
| 2014/0140653 | A1 | 5/2014 | Brown et al. |
| 2014/0140654 | A1 | 5/2014 | Brown et al. |
| 2014/0184699 | A1 | 7/2014 | Ito et al. |
| 2014/0204455 | A1 | 7/2014 | Popovich et al. |
| 2014/0361957 | A1 | 12/2014 | Hua et al. |
| 2015/0185475 | A1 | 7/2015 | Saarikko et al. |
| 2015/0289762 | A1 | 10/2015 | Popovich et al. |

FOREIGN PATENT DOCUMENTS

| | | |
|---|---|---|
| JP | 61213802 | 9/1986 |
| WO | 2010057219 A1 | 5/2010 |
| WO | 2013049012 A1 | 4/2013 |
| WO | 2013167864 A1 | 11/2013 |
| WO | 2013175465 A1 | 11/2013 |

OTHER PUBLICATIONS

U.S. Appl. No. 14/456,512, filed Aug. 11, 2014.
Honig, Zach, "Vuzix Designs Smart Glasses to Look Like Sunshades, Tout Connected Transparent Display", Published on: Jan. 7, 2012, Available at: http://www.engadget.com/2012/01/07/vuzix-smart-glasses-ces-2012/.
Massenot et al, "Multiplexed Holographic Transmission Gratings Recorded in Holographic Polymer-Dispersed Liquid Crystals: Static and Dynamic Studies", Applied Optics, vol. 44, Issue 25, Sep. 2005.
Zharkova et al., "Study of the Dynamics of Transmission Gratings Growth on Holographic Polymer-Dispersed Liquid Crystals", International Conference on Methods of Aerophysical Research, ICMAR, Aug. 2008.
Yan et al., "Multiplexing Holograms in the Photopolymer with Equal Diffraction Efficiency," Advances in Optical Data Storage Technology, Proceedings of SPIE, vol. 5643, (SPIE, Bellingham, WA), Jan. 2005.
Pu et al., "Exposure Schedule for Multiplexing Holograms in Photopolymer Films," Opt. Eng. 35(10), Oct. 1996.
Han et al., "Accurate Diffraction Efficiency Control for Multiplexed Volume Holographic Gratings", Opt. Eng. 41, Nov. 2002.
Minier et al., "Diffraction Characteristics of Superimposed Holographic Gratings in Planar Optical Waveguides", IEEE Photonics Technology Letters, vol. 4, No. 10, Oct. 1992.
Kress et al., "Exit Pupil Expander for Wearable See-Through Displays", Photonic Applications for Aerospace, Transportation, and Harsh Environment III, Proc. of SPIE vol. 8368, 83680D, May 1, 2012.
International Search Report and Written Opinion dated Mar. 18, 2015, in International Patent Application No. PCT/US2014/066999 filed Nov. 24, 2014.
International Search Report & Written Opinion dated Oct. 29, 2015, in International Application No. PCT/US2015/044400 filed Aug. 10, 2015.
Office Action dated Oct. 14, 2015, in U.S. Appl. No. 14/456,512, filed Aug. 11, 2014.
Response to Office Action filed Jan. 14, 2016, in U.S. Appl. No. 14/456,512, filed Aug. 11, 2014.
Notice of Allowance dated Mar. 2, 2016, in U.S. Appl. No. 14/456,512, filed Aug. 11, 2014.
U.S. Appl. No. 14/140,987, filed Dec. 26, 2013.
Mukawa et al., "8.4: Distinguished Paper: A Full Color Eyewear Display using Holographic Planar Waveguides", Information Technology Laboratories, Sony Corporation, Tokyo, Japan, May 2008, SID 08 Digest pp. 89-92.

(56) References Cited

OTHER PUBLICATIONS

Office Action dated Feb. 28, 2014, in U.S. Appl. No. 14/140,987, filed Dec. 26, 2013.
Response to Office Action filed May 15, 2014, in U.S. Appl. No. 14/140,987, filed Dec. 26, 2013.
Office Action dated Sep. 18, 2014, in U.S. Appl. No. 14/140,987, filed Dec. 26, 2013.
"Light focusing by chirped waveguide grating coupler," by Kumar et al, Proceeding of SPIE, vol. 8032, pp. 803203-1 through 803203-8, 2011.
Response to Office Action filed Dec. 3, 2014, in U.S. Appl. No. 14/140,987, filed Dec. 26, 2013.
Office Action dated Jan. 7, 2015, in U.S. Appl. No. 14/140,987, filed Dec. 26, 2013.
Response to Office Action filed Apr. 7, 2015, in U.S. Appl. No. 14/140,987, filed Dec. 26, 2013.
Office Action dated Jul. 6, 2015, in U.S. Appl. No. 14/140,987, filed Dec. 26, 2013.
Response to Office Action filed Oct. 6, 2015, in U.S. Appl. No. 14/140,987, filed Dec. 26, 2013.
Office Action dated Nov. 19, 2015, in U.S. Appl. No. 14/140,987, filed Dec. 26, 2013.
Response to Office Action filed Feb. 19, 2016, in U.S. Appl. No. 14/140,987, filed Dec. 26, 2013.
Notice of Allowance dated Jun. 3, 2016, in U.S. Appl. No. 14/140,987, filed Dec. 26, 2013.
Amendment dated Jun. 28, 2017, in European Patent Application No. 15778425.7 filed Sep. 16, 2015.

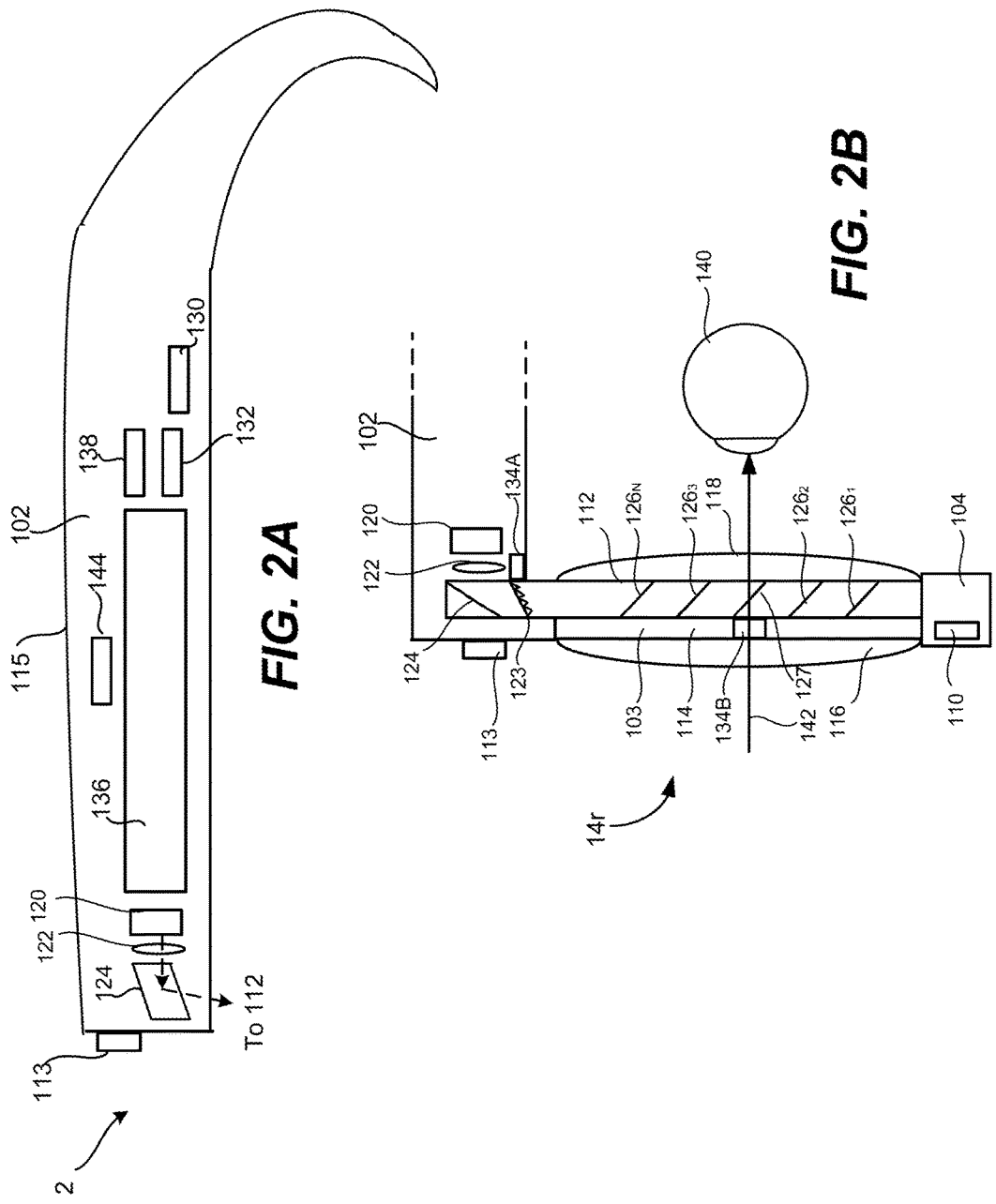

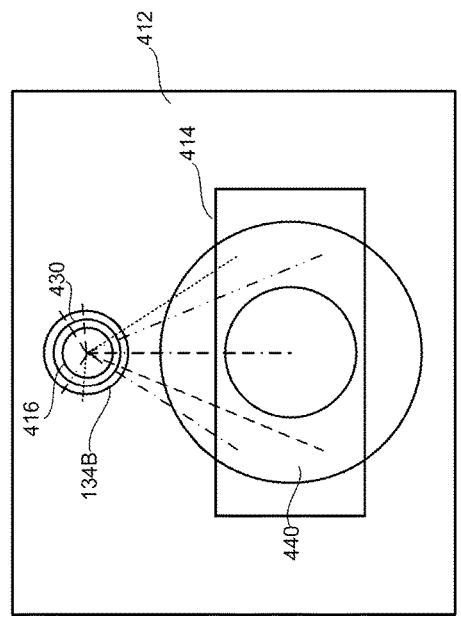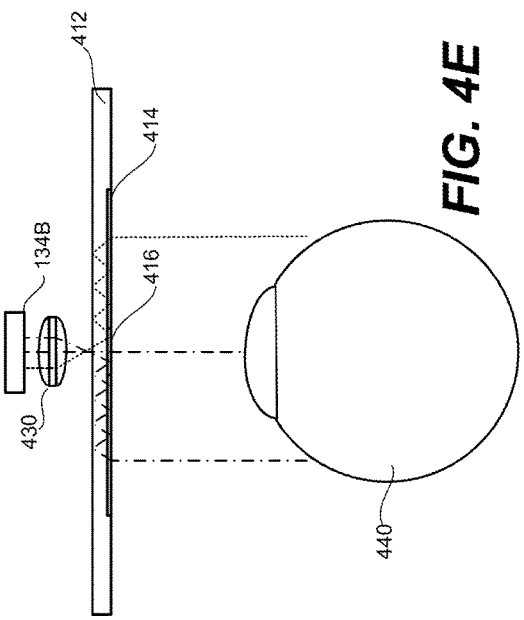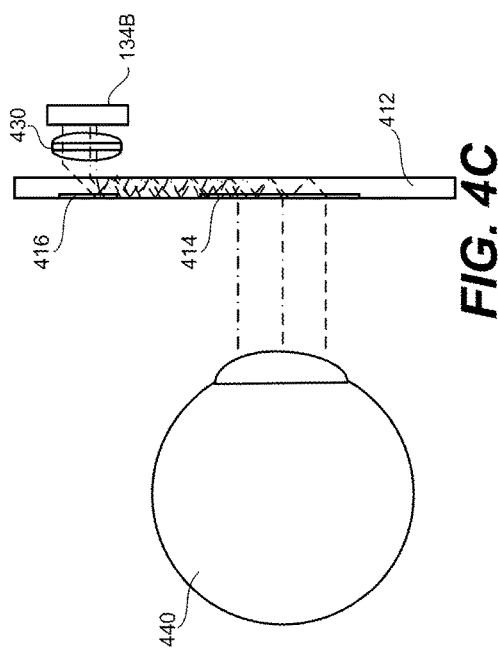

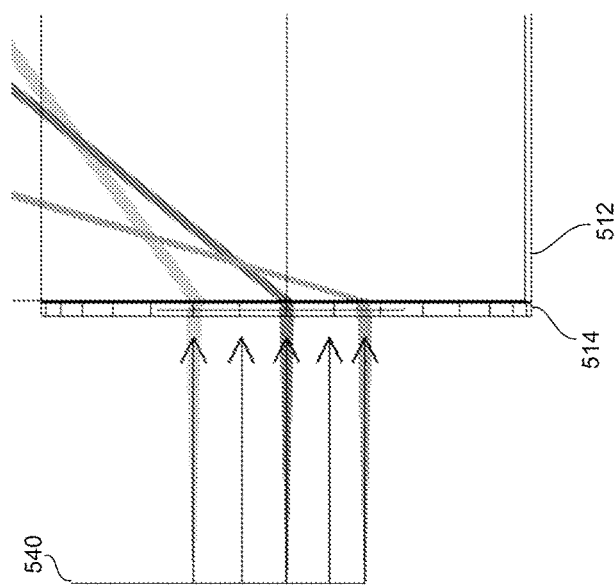
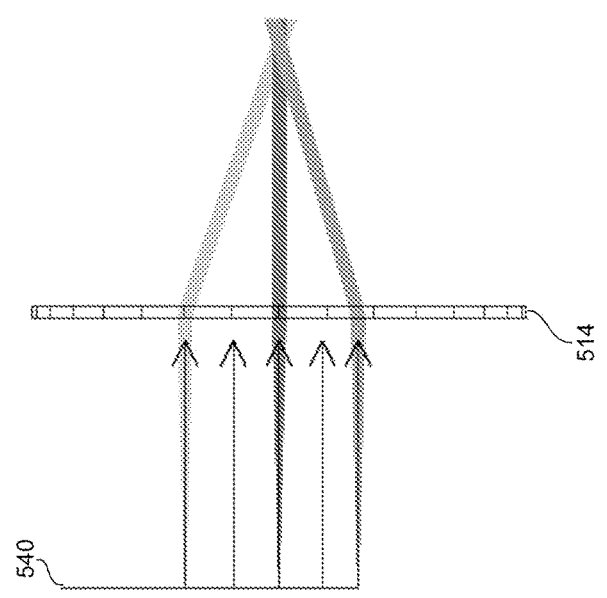
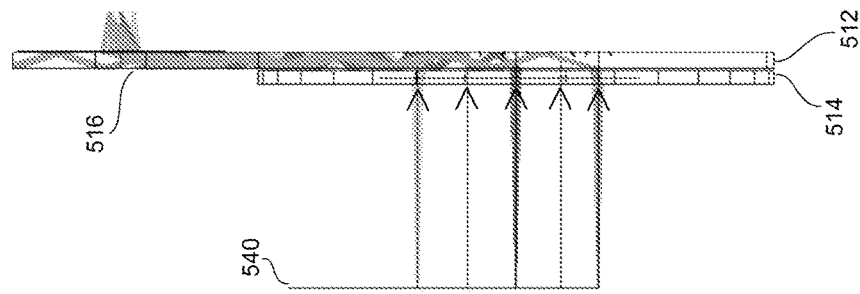

EYE TRACKING APPARATUS, METHOD AND SYSTEM

PRIORITY CLAIM

The present application is a continuation of and claims priority to U.S. patent application Ser. No. 14/140,987, filed Dec. 26, 2014, which is incorporated herein by reference.

BACKGROUND

A see-through, mixed reality display device system enables a user to observe digital information overlaid on the physical scenery. To enable hands-free user interaction, a see-through, mixed reality display device system may further be equipped with an eye tracker. Typically, an eye tracker includes an infrared (IR) light source to illuminate the user's eye and a camera to image the user's eye, e.g., to observe the reflected glints and iris movements for calculation of a gaze direction. The illumination and the imaging of the eye are preferably implemented such that: the see-through properties of the mixed reality display device system are not impaired by the eye tracking hardware; imaging of the eye works with all types of prescription spectacles; and imaging of the eye covers the entire eye movement range plus an inter-pupillary distance range.

One way to image an eye for eye tracking is using a simple camera mounted on the frame of a head mounted display (HMD) device, wherein the camera is directly focused on the user's eye. In other words, there is a direct line of sight from the camera to the eye. While such a configuration is relatively simple and inexpensive, it is highly sensitive to the position and movement of the camera relative to the eye. Also, with such a configuration the camera needs to be positioned close to the eye level, which typically causes at least partial obstruction of the see-through properties of the mixed reality display device system. Alternatively, a partial reflector may be used to fold the camera view path to the user's temple. While this alternative configuration allows the camera to be positioned outside the see-through field, implementation of this alternative configuration is problematic if the eye tracking needs to work with prescription eyewear.

Another possibility is to use a reverse optical path imaging in a free form prism based mixed reality display device system. This technique relies on the actual display optics to also provide the imaging functionality for eye tracking. However, because components of a free form prism tend to be rather large in size, this approach is not always practical. Adding a free form optical for eye tracking only is also possible, but this would be expensive and would add significant weight and size to the system.

SUMMARY

Certain embodiments described herein relate to a waveguide that is for use in tracking an eye that is illuminated by infrared light. Such a waveguide, which can be used in a head mounted display (HMD), but is not limited for use therewith, is transparent and includes an input-coupler and an output-coupler. The input-coupler comprises a grating area, formed by plurality of curved grating lines, that diffract light beams incident on the input-coupler into the waveguide and towards a common region at which is located the output-coupler. The curved grating lines of the input-coupler have a radially varying pitch. In accordance with an embodiment the radially varying pitch of the curved grating lines of the input-coupler decreases with increasing distance from the output-coupler. Preferably, the input-coupler and the output-coupler are positioned relative to one another to substantially achieve telecentricity. The output-coupler can comprise a linear grating, a holographic grating or a prism, but is not limited thereto.

When the input-coupler is positioned in front of an eye that is illuminated with infrared light, infrared light beams reflected from the eye and incident on the input-coupler enter the waveguide at the input-coupler, propagate through the waveguide from the input-coupler to the output-coupler by way of total internal reflections, and exit the waveguide proximate the output-coupler. The radially varying pitch of the curved grating lines of the input-coupler causes different beams of infrared light that are incident on respective different horizontal and vertical positions of the input-coupler to propagate through the waveguide at respective different angles of reflection and exit the waveguide at respective different angles of incidence relative to a surface of the waveguide through which the light beams exit.

The plurality of curved grating lines of the input-coupler each have a point of convergence that is located within the region of the waveguide at which is located the output-coupler. In a specific embodiment, the plurality of curved grating lines of the input-coupler are substantially concentric, each have substantially the same center of curvature, and each have substantially the same point of convergence. In an alternative embodiment, an optical transfer function of the input-coupler is substantially equivalent to an optical transfer function of an on-axis holographic lens combined with an optical transfer function of a linear diffraction grating. In this alternative embodiment, while the plurality of curved grating lines of the input-coupler are not substantially concentric, do not share substantially the same center of curvature, and do not share substantially the same point of convergence, the plurality of curved grating lines of the input-coupler will still each have a point of convergence that is located within the region of the waveguide at which is located the output-coupler.

In accordance with an embodiment, a system including an embodiment of the above summarized waveguide can also include an infrared illumination source that produces infrared light that is used to illuminate an eye. Such a system can also include a lens module that converts the infrared light beams that exit the waveguide from angularly encoded infrared light beams to two-dimensional spatially encoded infrared light beams. Additionally, such a system can include an sensor that produces eye tracking data in dependence on the two-dimensional spatially encoded infrared light beams produced using the lens module. Further, a system can include a processor that controls or modifies an aspect of an application based on the eye tracking data.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 2A is a side view of an eyeglass temple of the frame in an embodiment of the see-through, mixed reality display device embodied as eyeglasses providing support for hardware and software components.

FIG. 2B is a top view of an embodiment of an integrated eye tracking and display optical system of a see-through, near-eye, mixed reality device.

FIGS. 4C, 4D and 4E are side, front and top views, respectively, of the planar waveguide introduced in FIG. 4A, which also show a lens module and an eye tracking IR sensor for use with the planar waveguide.

FIGS. 5A-5C are used to illustrate a technique for designing an input-coupler for a planar waveguide, according to an embodiment.

DETAILED DESCRIPTION

Certain embodiments of the present technology relate to waveguides that enable imaging of an eye, for the purpose of eye tracking, to be implemented without impairing the see-through properties of a mixed reality display device system. Additionally, such embodiments can advantageously be used with prescription eyewear. Further, such embodiments can be used to perform imaging of the eye that covers the entire eye movement range plus an inter-pupillary distance range. However, before discussing such embodiments in additional detail, it is first useful to describe an exemplary see-through, mixed reality display device system with which embodiments of the present technology can be used.

Figure 1:
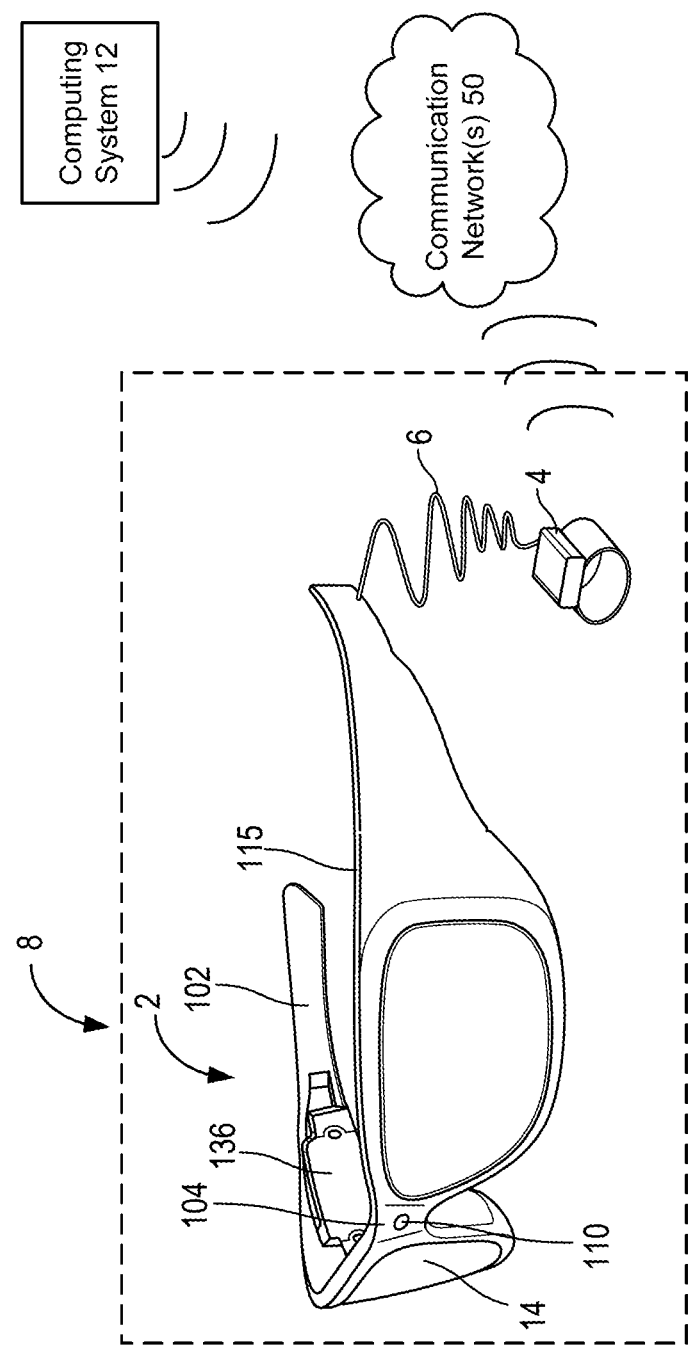
FIG. 1 is a block diagram depicting example components of one embodiment of a see-through, mixed reality display device system.

FIG. 1 is a block diagram depicting example components of one embodiment of a see-through, mixed reality display device system. System 8 includes a see-through display device as a near-eye, head mounted display device 2 in communication with processing unit 4 via wire 6. In other embodiments, head mounted display device 2 communicates with processing unit 4 via wireless communication. Processing unit 4 may take various embodiments. For example, processing unit 4 may be embodied in a mobile device like a smart phone, tablet or laptop computer. In some embodiments, processing unit 4 is a separate unit which may be worn on the user's body, e.g. the wrist in the illustrated example or in a pocket, and includes much of the computing power used to operate near-eye display device 2. Processing unit 4 may communicate wirelessly (e.g., WiFi, Bluetooth, infrared, RFID transmission, wireless Universal Serial Bus (WUSB), cellular, 3G, 4G or other wireless communication means) over a communication network 50 to one or more hub computing systems 12 whether located nearby in this example or at a remote location. In other embodiments, the functionality of the processing unit 4 may be integrated in software and hardware components of the display device 2.

Head mounted display device 2, which in one embodiment is in the shape of eyeglasses in a frame 115, is worn on the head of a user so that the user can see through a display, embodied in this example as a display optical system 14 for each eye, and thereby have an actual direct view of the space in front of the user.

The use of the term "actual direct view" refers to the ability to see real world objects directly with the human eye, rather than seeing created image representations of the objects. For example, looking through glass at a room allows a user to have an actual direct view of the room, while viewing a video of a room on a television is not an actual direct view of the room. Based on the context of executing software, for example, a gaming application, the system can project images of virtual objects, sometimes referred to as virtual images, on the display that are viewable by the person wearing the see-through display device while that person is also viewing real world objects through the display.

Frame 115 provides a support for holding elements of the system in place as well as a conduit for electrical connections. In this embodiment, frame 115 provides a convenient eyeglass frame as support for the elements of the system discussed further below. In other embodiments, other support structures can be used. An example of such a structure is a visor or goggles. The frame 115 includes a temple or side arm for resting on each of a user's ears. Temple 102 is representative of an embodiment of the right temple and includes control circuitry 136 for the display device 2. Nose bridge 104 of the frame 115 includes a microphone 110 for recording sounds and transmitting audio data to processing unit 4.

FIG. 2A is a side view of an eyeglass temple 102 of the frame 115 in an embodiment of the see-through, mixed reality display device embodied as eyeglasses providing support for hardware and software components. At the front of frame 115 is physical environment facing or outward facing video camera 113 that can capture video and still images which are transmitted to the processing unit 4.

The data from the camera may be sent to a processor 210 of the control circuitry 136, or the processing unit 4 or both, which may process them but which the unit 4 may also send to one or more computer systems 12 over a network 50 for processing. The processing identifies and maps the user's real world field of view.

Control circuits 136 provide various electronics that support the other components of head mounted display device 2. More details of control circuits 136 are provided below with respect to FIG. 3A. Inside, or mounted to the temple 102, are ear phones 130, inertial sensors 132, GPS transceiver 144 and temperature sensor 138. In one embodiment, inertial sensors 132 include a three axis magnetometer 132A, three axis gyro 132B and three axis accelerometer 132C (See FIG. 3A). The inertial sensors are for sensing position, orientation, and sudden accelerations of head mounted display device 2. From these movements, head position may also be determined.

Mounted to or inside the temple 102 is an image source or image generation unit 120. In one embodiment, the image source includes micro display 120 for projecting images of one or more virtual objects and lens system 122 for directing images from micro display 120 into a see-through planar waveguide 112. Lens system 122 may include one or more lenses. In one embodiment, lens system 122 includes one or more collimating lenses. In the illustrated example, a reflecting element 124 receives the images directed by the lens system 122 and optically couples the image data into the planar waveguide 112.

There are different image generation technologies that can be used to implement micro display 120. For example, micro display 120 can be implemented using a transmissive projection technology where the light source is modulated by optically active material, backlit with white light. These technologies are usually implemented using LCD type displays with powerful backlights and high optical energy densities. Micro display 120 can also be implemented using a reflective technology for which external light is reflected and modulated by an optically active material. Digital light processing (DLP), liquid crystal on silicon (LCOS) and Mirasol® display technology from Qualcomm, Inc. are all examples of reflective technologies. Additionally, micro display 120 can be implemented using an emissive technology where light is generated by the display, see for example, a PicoP™ display engine from Microvision, Inc. Another example of emissive display technology is a micro organic light emitting diode (OLED) display. Companies eMagin and Microoled provide examples of micro OLED displays.

FIG. 2B is a top view of an embodiment of a display optical system 14 of a see-through, near-eye, augmented or mixed reality device. A portion of the frame 115 of the near-eye display device 2 will surround a display optical system 14 for providing support for one or more optical elements as illustrated here and in the following figures and for making electrical connections. In order to show the components of the display optical system 14, in this case 14r for the right eye system, in the head mounted display device 2, a portion of the frame 115 surrounding the display optical system is not depicted.

In one embodiment, the display optical system 14 includes a planar waveguide 112, an optional opacity filter 114, see-through lens 116 and see-through lens 118. In one embodiment, opacity filter 114 is behind and aligned with see-through lens 116, planar waveguide 112 is behind and aligned with opacity filter 114, and see-through lens 118 is behind and aligned with planar waveguide 112. See-through lenses 116 and 118 may be standard lenses used in eye glasses and can be made to any prescription (including no prescription). In some embodiments, head mounted display device 2 will include only one see-through lens or no see-through lenses. Opacity filter 114, which is aligned with planar waveguide 112, selectively blocks natural light, either uniformly or on a per-pixel basis, from passing through planar waveguide 112. For example, the opacity filter enhances the contrast of the virtual imagery. More details of an opacity filter are provided in U.S. Patent Application Publication No. 2012/0068913, entitled "Opacity Filter For See-Through Mounted Display," filed on Sep. 21, 2010, by Bar-Zeev et al, which is incorporated herein by reference.

The planar waveguide 112 transmits visible light from micro display 120 to the eye 140 of the user wearing head mounted display device 2. The see-through planar waveguide 112 also allows visible light from in front of the head mounted display device 2 to be transmitted through itself 112 to eye 140, as depicted by arrow 142 representing an optical axis of the display optical system 14r, thereby allowing the user to have an actual direct view of the space in front of head mounted display device 2 in addition to receiving a virtual image from the micro display 120. Thus, the walls of planar waveguide 112 are see-through. Planar waveguide 112 includes a first reflecting surface 124 (e.g., a mirror or other surface). Visible light from micro display 120 passes through lens 122 and becomes incident on reflecting surface 124. The reflecting surface 124 reflects the incident visible light from the micro display 120 such that visible light is trapped inside a planar, substrate comprising planar waveguide 112 by internal reflection as described further below.

Infrared illumination and reflections also traverse the planar waveguide 112 for an eye tracking system 134 for tracking the position of the user's eyes. A user's eyes will be directed at a subset of the environment which is the user's area of focus or gaze. The eye tracking system 134 comprises an eye tracking illumination source 134A, which in this example is mounted to or inside the temple 102, and an eye tracking IR sensor 134B, which is this example is mounted to or inside a brow 103 of the frame 115. The eye tracking IR sensor 134B can alternatively be positioned between lens 118 and the temple 102. It is also possible that both the eye tracking illumination source 134A and the eye tracking IR sensor 134B are mounted to or inside the brow 103 of the frame 115.

The technology allows flexibility in the placement of entry and exit optical couplings (which can also be referred to as input- and output-couplers) to and from the waveguide's optical path for the image generation unit 120, the illumination source 134A and the eye tracking IR sensor 134B. The visible illumination representing images and the infrared illumination may enter from any direction about the waveguide 112, and one or more wavelength selective filters (e.g. 127) direct the illumination out of the waveguide centered about the optical axis 142 of the display optical system 14.

In one embodiment, the eye tracking illumination source 134A may include one or more infrared (IR) emitters such as an infrared light emitting diode (LED) or a laser (e.g. VCSEL) emitting about a predetermined IR wavelength or a range of wavelengths. In some embodiments, the eye tracking IR sensor 134B may be an IR camera or an IR position sensitive detector (PSD) for tracking glint positions.

In an embodiment, a wavelength selective filter 123 passes through visible spectrum light from the micro display 120 via reflecting surface 124 and directs the infrared wavelength illumination from the eye tracking illumination source 134A into the planar waveguide 112 where the IR illumination is internally reflected within the waveguide until reaching another wavelength selective filter 127 aligned with the optical axis 142.

From the IR reflections, the position of the pupil within the eye socket can be identified by known imaging techniques when the eye tracking IR sensor 134B is an IR camera, and by glint position data when the eye tracking IR sensor 134B is a type of position sensitive detector (PSD). The use of other types of eye tracking IR sensors and other techniques for eye tracking are also possible and within the scope of an embodiment.

After coupling into the waveguide 112, the visible illumination representing the image data from the micro display 120 and the IR illumination are internally reflected within the waveguide 112. In the example of FIG. 2B, after several reflections off the surfaces of the substrate, the trapped visible light waves reach an array of wavelength selective filters embodied in this example as selectively reflecting surfaces $126_1$ to $126_N$. Additionally, a wavelength selective filter 127 aligned with the optical axis of the display optical system is also positioned in the waveguide 112. Reflecting surfaces 126 couple visible light wavelengths incident upon those reflecting surfaces out of the substrate directed in the direction of the eye 140 of the user.

The reflecting surfaces 126 also pass infrared radiation within the waveguide. However, aligned with the optical axis 142 of the display optical system 14r, is one or more wavelength selective filters 127 which direct not only visible illumination but received infrared illumination from the illumination source 134A. For example, if the reflecting elements $126_1$ to $126_N$ are each reflecting different portions of the visible spectrum, the one or more wavelength selective filters 127 may reflect wavelengths in the red visible spectrum and the infrared spectrum. In other embodiments, the filters 127 can reflect wavelengths covering the entire visible spectrum or a larger portion thereof and the infrared spectrum for wavelengths of IR reflections and those generated by the IR illumination source.

Additionally, as will be discussed in more detail below with reference FIGS. 4A-5C an input-coupler (not specifically shown in FIGS. 2A and 2B, but shown in FIGS. 4A-5C) directs infrared reflections from the eye which pass through the see-through walls of the planar waveguide centered about the optical axis 142 into an optical path of the planar waveguide in a direction towards an output-coupler (not specifically shown in FIGS. 2A and 2B, but shown in FIGS. 4A-5C) that directs infrared light towards the eye tracking IR sensor 134B. Additionally, visible and infrared filters may be stacked in the direction from lens 116 to 118 so that they are all co-axial with the optical axis. For example, a bidirectional hot mirror placed in front of a visible reflecting element with respect to the eye lets visible light pass but reflects IR wavelengths. Additionally, the one or more filters 127 may be embodied as an active grating which is modulated between filtering wavelengths in the visible and infrared spectrums. This would be done at a rate fast enough for the human eye not to detect.

In one embodiment, each eye will have its own planar waveguide 112. When the head mounted display device has two planar waveguides, each eye can have its own micro display 120 that can display the same image in both eyes or different images in the two eyes. Further, when the head mounted display device has two planar waveguides, each eye can have its own eye tracking illumination source 134A and its own eye tracking IR sensor 134B. In another embodiment, there can be one planar waveguide with two optical axes, one for each eye, which spans the nose bridge and reflects visible and infrared light into both eyes.

In the embodiments described above, the specific number of lenses shown are just examples. Other numbers and configurations of lenses operating on the same principles may be used. Additionally, FIGS. 2A and 2B only show half of the head mounted display device 2. A full head mounted display device would include, for example, another set of see through lenses 116 and 118, another opacity filter 114, another planar waveguide 112 with one or more wavelength selective filters 127, another micro display 120, another lens system 122 physical environment facing camera 113 (also referred to as outward facing or front facing camera 113), eye tracking assembly 134, earphone 130, filter 123 and temperature sensor 138. Additional details of an exemplary head mounted display 2 are provided in United States Patent Application Publication No. 2012/0092328, entitled "Fusing Virtual Content Into Real Content," filed Oct. 15, 2010, by Flaks et al., which is incorporated herein by reference.

Figure 3A:
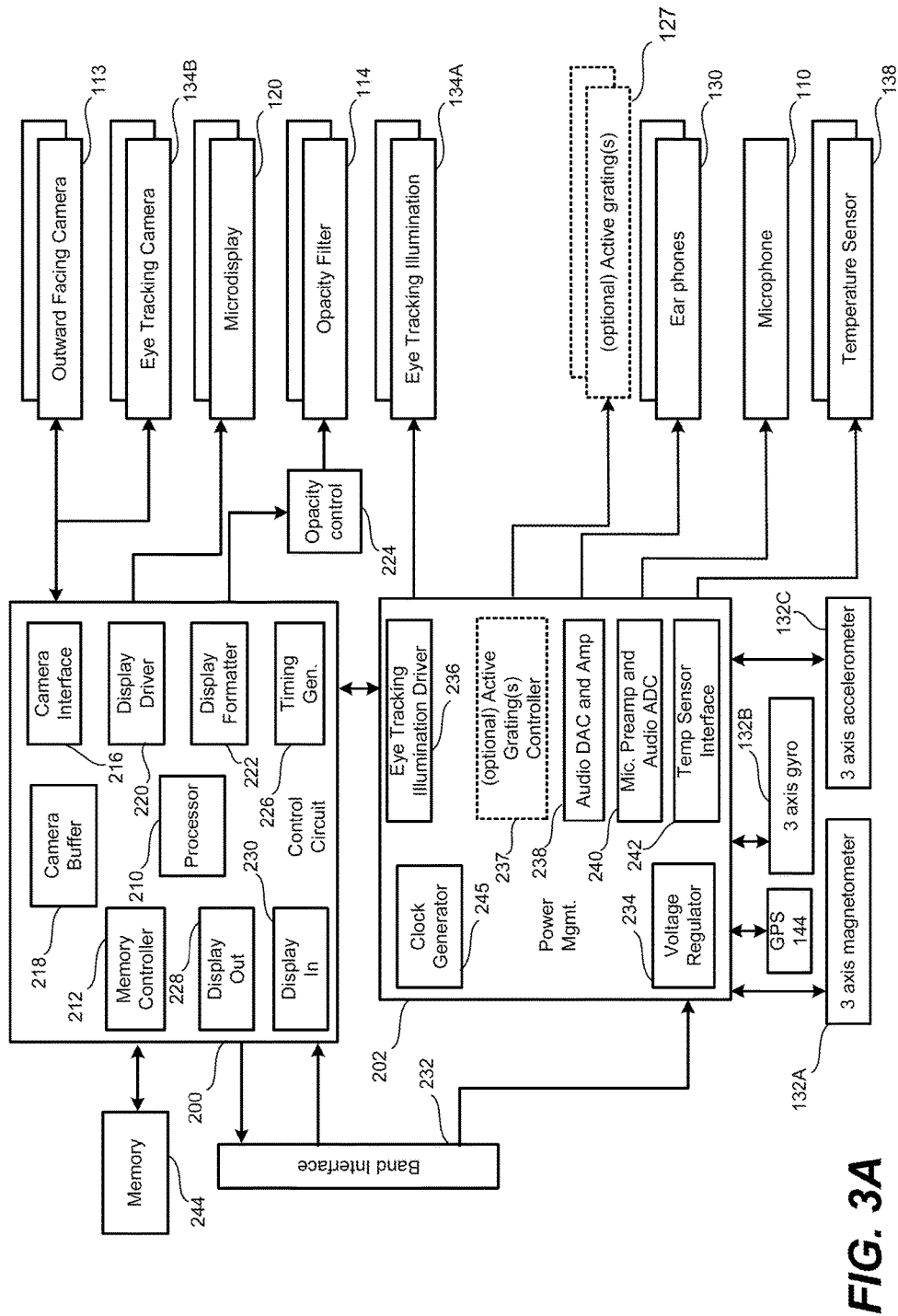
FIG. 3A is a block diagram of one embodiment of hardware and software components of a see-through, near-eye, mixed reality display device as may be used with one or more embodiments.
Figure 3B:
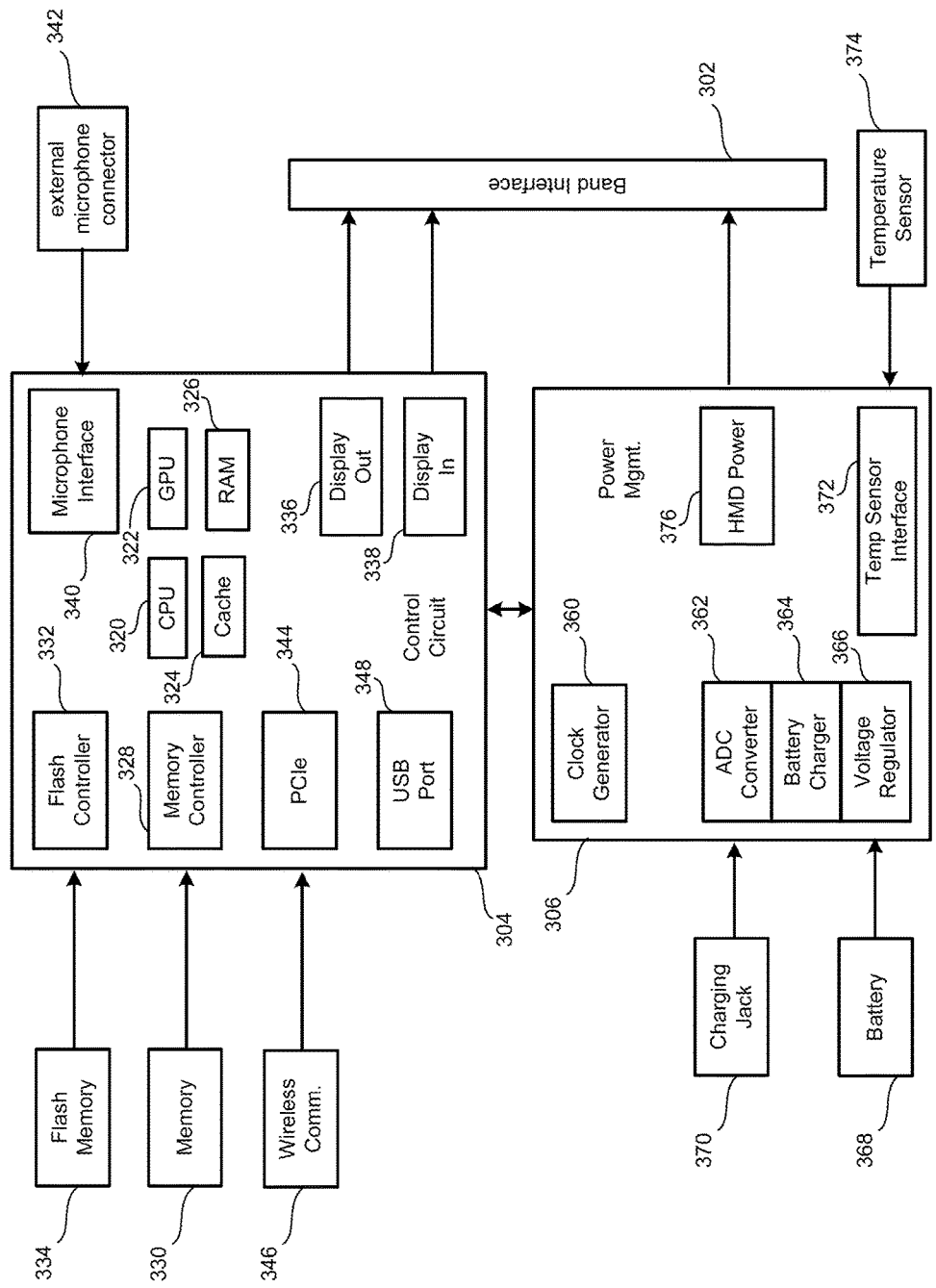
FIG. 3B is a block diagram describing the various components of a processing unit.

FIG. 3A is a block diagram of one embodiment of hardware and software components of a see-through, near-eye, mixed reality display device 2 as may be used with one or more embodiments. FIG. 3B is a block diagram describing the various components of a processing unit 4. In this embodiment, near-eye display device 2, receives instructions about a virtual image from processing unit 4 and provides data from sensors back to processing unit 4. Software and hardware components which may be embodied in a processing unit 4, for example as depicted in FIG. 3B, receive the sensory data from the display device 2 and may also receive sensory information from a computing system 12 over a network 50. Based on that information, processing unit 4 will determine where and when to provide a virtual image to the user and send instructions accordingly to the control circuitry 136 of the display device 2.

Note that some of the components of FIG. 3A (e.g., outward or physical environment facing camera 113, eye camera 134, micro display 120, opacity filter 114, eye tracking illumination unit 134A, earphones 130, one or more wavelength selective filters 127, and temperature sensor 138) are shown in shadow to indicate that there can be at least two of each of those devices, at least one for the left side and at least one for the right side of head mounted display device 2. FIG. 3A shows the control circuit 200 in communication with the power management circuit 202. Control circuit 200 includes processor 210, memory controller 212 in communication with memory 244 (e.g., D-RAM), camera interface 216, camera buffer 218, display driver 220, display formatter 222, timing generator 226, display out interface 228, and display in interface 230. In one embodiment, all of components of control circuit 200 are in communication with each other via dedicated lines of one or more buses. In another embodiment, each of the components of control circuit 200 is in communication with processor 210.

Camera interface 216 provides an interface to the two physical environment facing cameras 113 and, in this embodiment, an IR camera as sensor 134B and stores respective images received from the cameras 113, 134B in camera buffer 218. Display driver 220 will drive microdisplay 120. Display formatter 222 may provide information, about the virtual image being displayed on microdisplay 120 to one or more processors of one or more computer systems, e.g. 4 and 12 performing processing for the mixed reality system. The display formatter 222 can identify to the opacity control unit 224 transmissivity settings with respect to the display optical system 14. Timing generator 226 is used to provide timing data for the system. Display out interface 228 includes a buffer for providing images from physical environment facing cameras 113 and the eye cameras 134B to the processing unit 4. Display in interface 230 includes a buffer for receiving images such as a virtual image to be displayed on microdisplay 120. Display out 228 and display in 230 communicate with band interface 232 which is an interface to processing unit 4.

Power management circuit 202 includes voltage regulator 234, eye tracking illumination driver 236, audio DAC and amplifier 238, microphone preamplifier and audio ADC 240, temperature sensor interface 242, active filter controller 237, and clock generator 245. Voltage regulator 234 receives power from processing unit 4 via band interface 232 and provides that power to the other components of head mounted display device 2. Illumination driver 236 controls, for example via a drive current or voltage, the eye tracking illumination unit 134A to operate about a predetermined wavelength or within a wavelength range. Audio DAC and amplifier 238 provides audio data to earphones 130. Microphone preamplifier and audio ADC 240 provides an interface for microphone 110. Temperature sensor interface 242 is an interface for temperature sensor 138. Active filter controller 237 receives data indicating one or more wavelengths for which each wavelength selective filter 127 is to act as a selective wavelength filter. Power management unit 202 also provides power and receives data back from three axis magnetometer 132A, three axis gyroscope 132B and three axis accelerometer 132C. Power management unit 202 also provides power and receives data back from and sends data to GPS transceiver 144.

FIG. 3B is a block diagram of one embodiment of the hardware and software components of a processing unit 4 associated with a see-through, near-eye, mixed reality display unit. FIG. 3B shows controls circuit 304 in communication with power management circuit 306. Control circuit 304 includes a central processing unit (CPU) 320, graphics processing unit (GPU) 322, cache 324, RAM 326, memory control 328 in communication with memory 330 (e.g., D-RAM), flash memory controller 332 in communication with flash memory 334 (or other type of non-volatile storage), display out buffer 336 in communication with see-through, near-eye display device 2 via band interface 302 and band interface 232, display in buffer 338 in communication with near-eye display device 2 via band interface 302 and band interface 232, microphone interface 340 in communication with an external microphone connector 342 for connecting to a microphone, PCI express interface for connecting to a wireless communication device 346, and USB port(s) 348.

In one embodiment, wireless communication component 346 can include a Wi-Fi enabled communication device, Bluetooth communication device, infrared communication device, cellular, 3G, 4G communication devices, wireless USB (WUSB) communication device, RFID communication device etc. The wireless communication component 346 thus allows peer-to-peer data transfers with for example, another display device system 8, as well as connection to a larger network via a wireless router or cell tower. The USB port can be used to dock the processing unit 4 to another display device system 8. Additionally, the processing unit 4 can dock to another computing system 12 in order to load data or software onto processing unit 4 as well as charge the processing unit 4. In one embodiment, CPU 320 and GPU 322 are the main workhorses for determining where, when and how to insert virtual images into the view of the user.

Power management circuit 306 includes clock generator 360, analog to digital converter 362, battery charger 364, voltage regulator 366, see-through, near-eye display power source 376, and temperature sensor interface 372 in communication with temperature sensor 374 (located on the wrist band of processing unit 4). An alternating current to direct current converter 362 is connected to a charging jack 370 for receiving an AC supply and creating a DC supply for the system. Voltage regulator 366 is in communication with battery 368 for supplying power to the system. Battery charger 364 is used to charge battery 368 (via voltage regulator 366) upon receiving power from charging jack 370. Device power interface 376 provides power to the display device 2.

Planar Waveguide

FIGS. 4A-4E will now be used to describe specific features of a planar waveguide 412, according to an embodiment of the present technology, wherein the waveguide 412 can be used to implement the waveguide 112 discussed above with reference to FIGS. 1, 2A and 2B. More specifically, FIGS. 4A-4E will be used to describe portions of the planar waveguide 412 that are used to collect infrared light reflected from an eye 440 and provide the infrared light to the eye tracking IR sensor 134B discussed above with reference to FIGS. 2B and 3A. Infrared light will be reflected from the eye 440, e.g., when the eye is illuminated by infrared light produced by the eye tracking illumination unit 134A, as explained above.

Figure 4A:
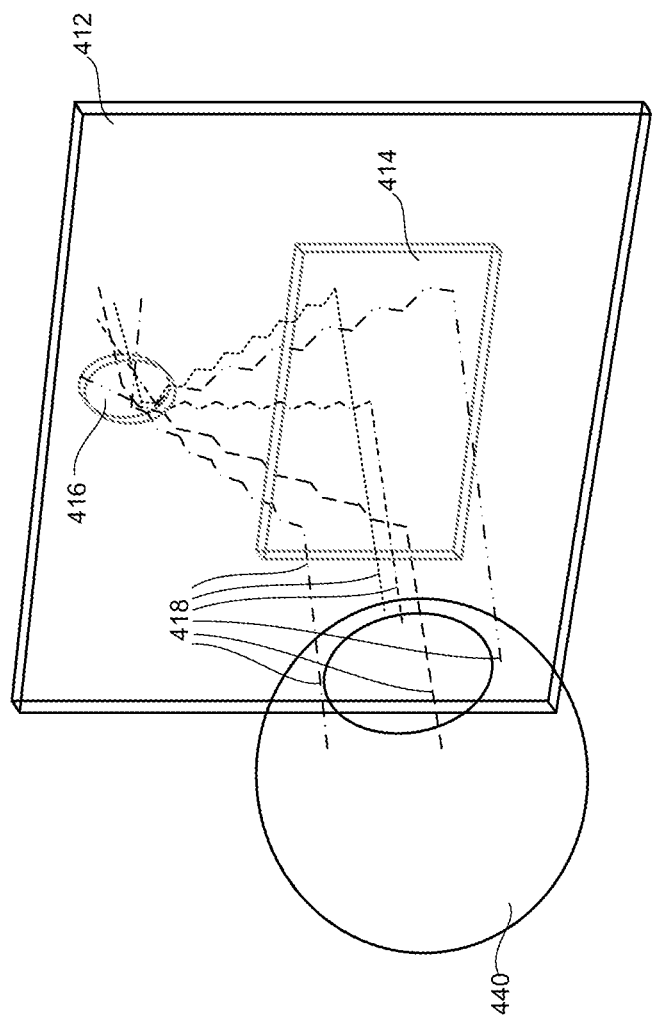
FIG. 4A is perspective view of a planar waveguide according to an embodiment.

FIG. 4A illustrates a perspective view of the planar waveguide 412. Referring to FIG. 4A, the planar waveguide 412 is shown as including an input-coupler 414 and an output-coupler 416. When the input-coupler 414 is positioned in front of an eye 440 that is illuminated with infrared light, infrared light beams (illustrated by dashed lines 418) reflected from the eye 440 and incident on the input-coupler 414 enter the waveguide 412 at the input-coupler 414, propagate through the waveguide 412 from the input-coupler 414 to the output-coupler 416 by way of total internal reflections, and exit the planar waveguide 412 proximate the output-coupler 416. The output-coupler 416 can be, e.g., a linear grating type of output-coupler, a holographic grating type of output-coupler, a prism or another optical coupler capable of causing infrared light (and/or light of other wavelengths) to exit the waveguide 412. The input-coupler 414 can be either a transmission type input-coupler or a reflective type input-coupler. Similarly, the output-coupler 416 can be either a transmission type output-coupler or a reflective type output-coupler. Depending upon implementation, features of the output-coupler can be included in either planar surface of the planar waveguide 412, or in both planar surfaces of the planar waveguide. Details of the input-coupler 414, according to a specific embodiment, are discussed below with reference to FIG. 4B.

Figure 4B:
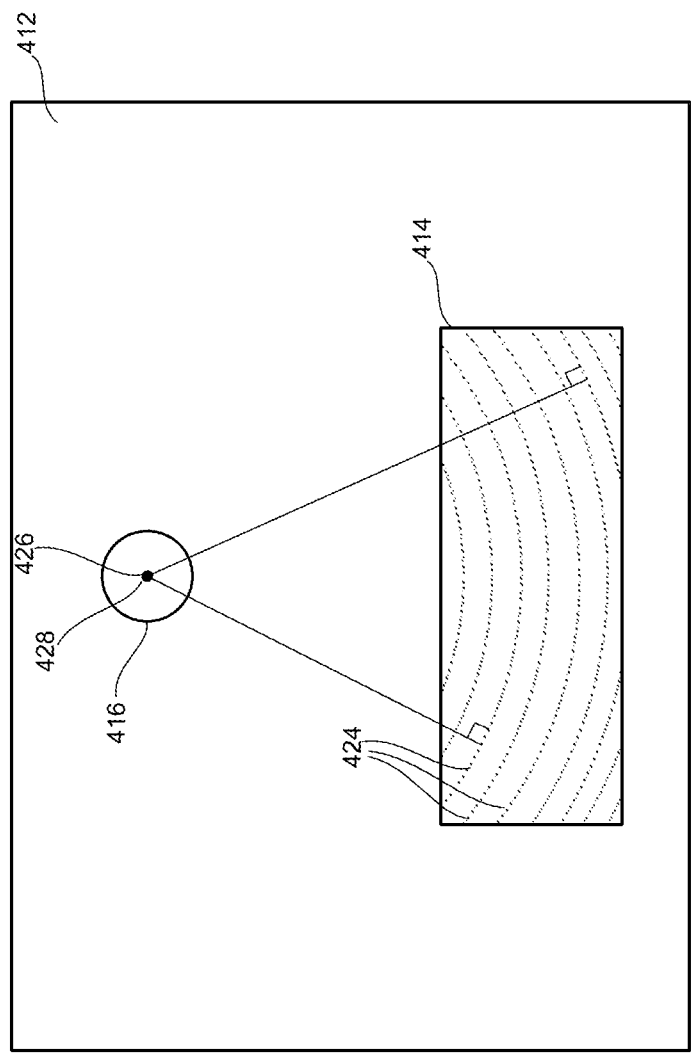
FIG. 4B is a front view of the planar waveguide introduced in FIG. 4A.

FIG. 4B, which is a front view of the planar waveguide 412 of FIG. 4A, illustrates that the input-coupler 414 includes a plurality of curved grating lines 424. Explained another way, the input-coupler 114 comprises a grating area formed by plurality of curved grating lines. In accordance with an embodiment, the plurality of curved grating lines 424 are concentric, each have the same center of curvature 426, and each have the same point of convergence 428. More specifically, in this particular embodiment, the center of curvature 426 and the point of converge 428 for each of the curved grating lines 424 are the same point, which is located at or near the center of the output-coupler 416. In this configuration, the curved grating lines 424 of the input-coupler 414 diffract light beams incident on the input-coupler 414 into the waveguide 412 and towards the region of the waveguide 414 at which is located the output-coupler 416. While only a few of the curved grating lines 424 are illustrated in FIG. 4B, the input-coupler 416 will likely include thousands or tens of thousands of the curved grating lines 424.

The plurality of curved grating lines 424 of the input-coupler 414 have a radially varying pitch, meaning that the distances between adjacent pairs of curved grating lines 424 change from one pair of adjacent curved grating lines 424 to the next. More specifically, the radially varying pitch of the curved grating lines 424 of the input-coupler 414 decreases with increases in distance between the curved grating lines 424 and the output-coupler 416. In other words, where a first pair of adjacent curved grating lines 424 is closer to the output-coupler 416 than a second pair of adjacent curved grating lines 424, a distance between the first pair of adjacent curved grating lines 424 will be greater than a distance between the second pair of adjacent curved grating lines 424. In accordance with an embodiment, the radially varying pitch of the curved grating lines 424 varies from about 500 nm to about 1 µm, but is not limited thereto. For example, the distance between the two curved grating lines 424 (of the input-coupler 414) that are closest to the output-coupler 416 can be about 1 µm, and the distance between the two curved grating lines 424 (of the input-coupler 414) that are farthest from the output-coupler 416 can be about 500 nm (i.e., about 0.5 µm). It can be appreciated from this description that the planar waveguide 412, the input-coupler 414, the curved grating lines 424 (of the input-coupler 414), and the output-coupler are not drawn to scale, but, rather, simply illustrate exemplary relatively locations of each of these elements relative to the other elements.

The radially varying pitch of the curved grating lines 424 (of the input-coupler 414) causes different beams of infrared light that are incident on different horizontal and vertical positions of the input-coupler 414 to propagate through the planar waveguide 412 at respective different angles of reflection, and exit the output-coupler 416 at respective different angles of incidence relative to the surface of the planar waveguide 412 through with the infrared light beams exit. Explained another way, the radially varying pitch of the curved grating lines 424 (of the input-coupler 414) cause angular encoding of the infrared light beams that are incident on the input-coupler 414, thereby enabling the infrared light beams that exit the planar waveguide 412 through the output-coupler 416 to be imaged (e.g., by the eye tracking IR sensor 134B) in a manner that distinguishes between infrared light beams that were incident on different horizontal and vertical positions of the input-coupler 414.

The curved grating lines 424 of the input-coupler 414 can be formed in various different manners. One way is to use a holographic approach to record the curved grating lines 424. Alternatively, the curved grating lines 424 can be formed using electron-beam lithography or photo-lithography. These are just a few examples of the various ways of forming the curved grating lines 424 of the input-coupler 414, which are not meant to be limiting. Depending upon implementation, the grating lines of the input-coupler 414 can be included in either planar surface of the planar waveguide, or in both planar surfaces of the planar waveguide.

In an embodiment, the input-coupler 414 and the output-coupler 416 are positioned relative to one another to achieve telecentricity. Under this circumstance, the entrance pupil is located at infinity, which makes the input-coupler object-space telecentric. This advantageously provides an orthographic projection of the eye 440.

Preferably, the infrared light beams that travel through the planar waveguide 412 are collimated, but some degree of non-collimation can be tolerated. The input-coupler 414 works as a focus element so that when the eye 440 is at a nominal eye relief distance, which is a focal distance of the input-coupler 414, the guided light naturally becomes collimated. More specifically, a ray bundle of infrared light generated from the same field point on the eye plane becomes collimated inside of the waveguide 412. However, due to the radial variable pitch of the curved grating lines 424, ray bundles from different field points on the eye plane will have different angles of incidence, which provides for the angular encoding mentioned above.

FIG. 4C, which illustrates a side view of the planar waveguide 412, also shows a lens module 430 located near the output-coupler 416. The lens module 430, which can include one or more lenses, is configured to convert the angular space of the rays within the planar waveguide 412 to two-dimensional (2D) space after the rays exit the planar waveguide 412 proximate the output-coupler 416. Explained another way, the lens module 430 is used to convert angular encoded infrared light beams into two-dimensional (2D) spatially encoded infrared light beams. After being converted to two-dimensional space, the infrared light beams are incident on a two-dimensional plane of the eye tracking IR sensor 134B, as shown in FIG. 4C. The eye tracking IR sensor 134B produces eye tracking data in dependence on the two-dimensional spatially encoded infrared light beams that are incident on the sensor.

FIG. 4D, which is another front view of the planar waveguide 412, is similar to FIG. 4B, but also shows locations of the lens module 430 and the eye tracking IR sensor 134B, relative to the output-coupler 416. However, FIG. 4D does not illustrate the curved grating lines 424 shown in FIG. 4B. Nevertheless, the input-coupler 414 does indeed include the curved grating lines described above. FIG. 4E is a top view of the planar waveguide 412, which also illustrates relative positions of the lens module 430 and the eye tracking IR sensor 134B, relative to the input-coupler 414 and the output-coupler 416.

The planar waveguide 412 can be incorporated into a see-through mixed reality display device system, such as the one described above with reference to FIGS. 1-3B, but is not limited to user therewith. As previously mentioned, the planar waveguide 412 can be used as the waveguide 112 discussed above with reference to FIG. 2B. Accordingly, the planar waveguide 412 may be positioned next to or between see-through lenses (e.g., 116 and/or 118), which may be standard lenses used in eye glasses and can be made to any prescription (including no prescription). The planar waveguide 412 can alternatively be used with any system that is intended to perform eye tracking based on infrared light reflected from an eye. In general, the input-coupler 414 of the planar waveguide is preferably axially aligned with the eye, such that when the eye is illuminated with infrared light, infrared light beams reflected from the eye will be incident on the input-coupler 414 of the planar waveguide 412. The output-coupler 416 is preferably located in close proximity to the sensor or camera (e.g., eye tracking IR sensor 134B) that is used to image the eye. As was mentioned above, such a sensor or camera can be mounted to or inside the brow (e.g., 103) of a frame (e.g., 115). Alternatively, a sensor or camera can be mounted to or inside the temple or side arm (e.g., 102) of a frame, in which case, the relative positions of the input-coupler 414 and the output-coupler 416 may be rotated by ninety degrees. As was explained above, a lens module (e.g., 430) can be located between the output-coupler 416 and the sensor (e.g., eye tracking IR sensor 134B).

In accordance with an embodiment, a way to design an input-coupler (e.g., 414) for a planar waveguide (e.g., 412) is to design two separate optical devices that collectively provide the functionality desired for the input-coupler. More specifically, the functionality of the input-coupler 414 can be provided collectively by an on-axis holographic lens and a linear diffractive grating, as will now be described with reference to FIGS. 5A-5C.

Referring to FIG. 5A-5C, the line 540 represents an eye plane, and the element 514 represents an on-axis holographic lens. In FIG. 5A, element 512 represents a planar waveguide that includes a linear diffractive grating in the portion of the waveguide 512 that is next to the on-axis holographic lens 514.

FIG. 5B is used to explain the functionality of the on-axis holographic lens 514, if it were by itself. More specifically, FIG. 5B illustrates that infrared light beams that are reflected from the eye plane 540 and are incident on the on-axis holographic lens 514 are focused to a common point. FIG. 5C, which includes a blown-up or magnified portion of the planar waveguide 512 that includes a linear diffraction grating, illustrates that the linear diffraction grating changes the direction of the light beams (that have traveled through the on-axis holographic lens 514) such that the light beams are diffracted into the waveguide 512 and towards the region of the waveguide 512 at which is located an output-coupler 516.

By designing the input-coupler as including an on-axis holographic lens 514 next to a linear diffractive grating, the input-coupler can be designed to increase and preferably maximize the vertical object height that can be imaged using the input-coupler. Once the design of the on-axis holographic lens and the linear diffractive grating are complete, those two components are mathematically reduced to a single diffractive optical element. This can be done by making an optical transfer function of the input-coupler substantially equivalent to an optical transfer function of the on-axis holographic lens combined with an optical transfer function of the linear diffraction grating.

Such a single diffractive optical element will be similar to, but not identical to, to the input-coupler 414 described with reference to FIGS. 4A-4E. For example, the resulting single diffractive optical element input-coupler will also include curved grating lines having a radially varying pitch, as was the case with the input-coupler 414. However, the plurality of curved grating lines in this embodiment will not all have the same center of curvature and point of convergence. Rather, the centers of curvature and points of convergence will blur-out somewhat, such that they are close to one another, but not at the same exact point. That is fine, so long as curved grating lines of the input-coupler each have a point of convergence that is located within the region of the waveguide at which is located the output-coupler 516. This will ensure that when the input-coupler is positioned in front of an eye that is illuminated with infrared light, infrared light beams reflected from the eye and incident on the input-coupler enter the waveguide at the input-coupler, propagate through the waveguide from the input-coupler to the output-coupler by way of total internal reflections, and exit the planar waveguide proximate the output-coupler 516.

Also, as was the case with the input-coupler 414 described with reference to FIGS. 4A-4E, the radially varying pitch of the curved grating lines of the input-coupler in this embodiment will cause different beams of infrared light that are incident on different horizontal and vertical positions of the input-coupler to propagate through the waveguide at respective different angles of reflection and exit the waveguide at respective different angles of incidence relative to a surface of the waveguide through which the infrared light beams exit. In other words, this embodiment also achieves angular encoding of the infrared light beams that are incident on the input-coupler. While not specifically shown in FIG. 5A, a lens module (e.g., 430) can be used to convert the infrared light beams that exit the planar waveguide 512 from angularly encoded infrared light beams to two-dimensional spatially encoded infrared light beams. Additionally, an eye tracking IR sensor (e.g., 134B) can produce eye tracking data in dependence on the two-dimensional spatially encoded infrared light beams produced using the lens module.

Figure 6:
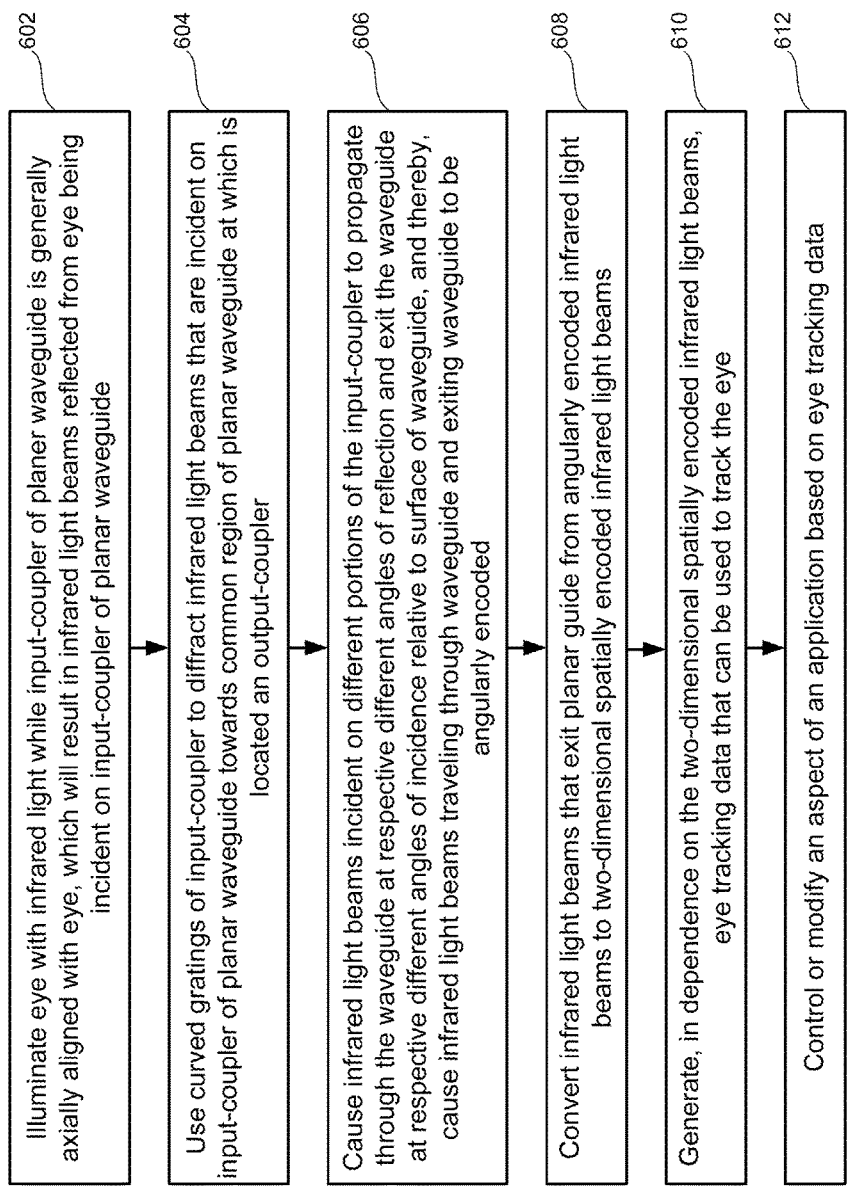
FIG. 6 is a high level flow diagram that is used to summarize a method for use in tracking an eye.

FIG. 6 is a flowchart that is used to summarize a method for use in eye tracking. Referring to FIG. 6, at step 602, an eye is illuminated with infrared light while an input-coupler of a planar waveguide is generally axially aligned with the eye, which will result in infrared light beams reflected from the eye being incident on the input-coupler of the planar waveguide.

As indicated at step 604, curved grating lines of the input-coupler cause infrared light beams that are incident on the input-coupler of the planar waveguide to be diffracted towards a common region of the planar waveguide at which is located an output-coupler. As indicated at step 606, infrared light beams incident on different portions of the input-coupler are caused to propagate through the waveguide at respective different angles of reflection and exit the waveguide at respective different angles of incidence relative to a surface of waveguide through which the infrared light beams exit. In other words, at step 606 there is angular encoding of the infrared light beams that are incident on, and enter the waveguide at, the input-coupler. Such angular encoding is achieved because of the radially varying pitch of the curved grating lines of the input-coupler, as was explained above. While steps 604 and 606 are shown as two separate steps, such steps are likely performed simultaneously.

As indicated at step 608, the infrared light beams that exit the planar waveguide are converted from angularly encoded infrared light beams to two-dimensional spatially encoded infrared light beams. As was explained above, this can be achieved using a lens module (e.g., 430).

As indicated at step 610, eye tracking data that can be used to track the eye is generated in dependence on the two-dimensional spatially encoded infrared light beams. As was explained above, this can be achieved using an eye tracking IR sensor (e.g., 134B). The sensor can be, e.g., a charge-coupled device (CCD) or CMOS pixel sensor array, but is not limited thereto. Some examples of eye tracking data are image data from an infrared camera or positions detected for glints by a position sensitive detector (PSD). Eye tracking data can be used, for example, to determine a point of gaze, which indicates one or more objects, real or virtual, at which a user is gazing. In other words, eye tracking data can be used to determine a direction or object at which the user is looking. Eye tracking, as is known in the art, can involve measuring vergence, inter-pupillary distance (IPD), gaze determination, eye movement based commands, biometric identification, but is not limited thereto.

The position of the pupil within the eye socket can be identified by known imaging techniques when the IR sensor is an IR camera, and by glint position data when the IR sensor is a type of position sensitive detector (PSD). For a more specific example, the position of the pupil can be identified by known imaging techniques which detects the reflection of the cornea, e.g., as disclosed in U.S. Pat. No. 7,401,920, entitled "Head Mounted Eye Tracking and Display System", issued Jul. 22, 2008 to Kranz et al., which is incorporated herein by reference. Such a technique can locate a position of the center of the eye relative to a tracking camera (e.g., eye tracking IR sensor 134B). Generally, eye tracking involves obtaining an image of the eye and using computer vision techniques to determine the location of the pupil within the eye socket. In one embodiment, it is sufficient to track the location of one eye since the eyes usually move in unison. However, it is also possible to track each eye separately. Where two eyes are being tracked, there can be a separate one of the planar waveguides described herein for each one of the eyes. Another example of a patent that describes techniques for tracking an eye based on reflected infrared light and generating eye tracking data is U.S. Pat. No. 8,487,838, entitled "Gaze Detection in a See-Through, Near-Eye, Mixed Reality Display," issued Jul. 16, 2013, to Lewis et al., which is also incorporated herein by reference.

As indicated at step 612, an aspect of an application is controlled or modified based on the eye tracking data. Step 612 can be performed, e.g., using a processor (e.g., 210 or 320). Step 612 can involve, for example, enabling a user to make a selection from a list, enabling a user to control how an avatar proceeds through a virtual environment, or causing certain virtual objects to be emphasized, but are not limited thereto. Step 612 can additionally, or alternatively, involve observing a user's reactions to certain visual stimuli, or the like.

The planar waveguides disclosed herein advantageously can be employed with eye tracking hardware in a manner that does not impair the see-through properties of the mixed reality display device system. Further, the planar waveguides disclosed herein enables imaging of the eye the works with all types of prescription spectacles, and enables imaging of the eye that covers the entire eye movement range plus an inter-pupillary distance range.

In the above description, the waveguide 412 was typically described as being a planar waveguide 412 that includes a pair of planar surfaces. In an alternative embodiment, one or both of the main surfaces of the waveguide could be non-planar, i.e., curved. While gratings may be more easily manufacture on or in planar surfaces, with curved surface(s) it could be possible to reduce some of the aberrations in the system.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the present technology. For example, it would be possible to combine or separate some of the steps shown in FIG. 6. For another example, it is possible to change the boundaries of some of the blocks shown in FIGS. 3A and 3B.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. It is intended that the scope of the technology be defined by the claims appended hereto.

What is claimed is:

1. An apparatus for use in tracking an eye that is illuminated by infrared light, the apparatus comprising:
a waveguide that is transparent and includes an input-coupler and an output-coupler that are spatially separated from one another; and
a light source adapted to illuminate an eye with infrared light so that at least a portion of the infrared light is reflected from the eye and is incident on the input-coupler;
wherein the input-coupler comprises a plurality of curved grating lines that are configured to diffract infrared light beams incident on the input-coupler into the waveguide and towards a common region at which is located the output-coupler by way of total internal reflections;
wherein the plurality of curved grating lines of the input-coupler have a radially varying pitch that decreases with increases in distances between the curved grating lines and the output-coupler;
wherein the plurality of curved grating lines of the input-coupler each have a respective center of curvature and a respective point of convergence that are located within the region of the waveguide at which is located the output-coupler; and
wherein the radially varying pitch of the plurality of curved grating lines of the input-coupler are configured to cause different infrared light beams that are incident on different horizontal and vertical positions of the input-coupler to propagate through the waveguide at respective different angles of reflection and exit the waveguide at respective different angles of incidence relative to a surface of the waveguide through which the infrared light beams exit.

2. The apparatus of claim 1, wherein for each point on each of the plurality of curved grating lines of the input-coupler the respective center of curvature is within the region of the waveguide at which is located the output-coupler.

3. The apparatus of claim 1, wherein the input-coupler is configured to cause ray bundles of infrared light reflected from a same field point on the eye that enter the waveguide through the input-coupler to become collimated inside of the waveguide and exit the waveguide with a same angle of incidence relative to a surface of the waveguide through which the infrared light exits, when the input-coupler is at a nominal eye relief distance, which is a focal distance of the input-coupler.

4. The apparatus of claim 1, wherein the input-coupler is configured to cause ray bundles of infrared light reflected from different field points on the eye to propagate through the waveguide at respective different angles of reflection and exit the waveguide with respective different angles of incidence relative to a surface of the waveguide through which the infrared light exits to thereby provide for angular encoding of infrared light that is reflected off different field points on the eye, when the input-coupler is at a nominal eye relief distance, which is a focal distance of the input-coupler.

5. The apparatus of claim 1, wherein when the input-coupler is positioned in front of an eye that is illuminated with infrared light, infrared light beams reflected from the eye and incident on the input-coupler enter the waveguide at the input-coupler, propagate through the waveguide from the input-coupler to the output-coupler by way of total internal reflections, and exit the waveguide proximate the output-coupler.

6. The apparatus of claim 1, wherein:
the radially varying pitch of the curved grating lines of the input-coupler varies within a range that is between about 500 nm and 1000 nm, with the radially varying pitch being greatest closest to the output coupler and decreasing with increases in distances between the curved grating lines and the output-coupler.

7. The apparatus of claim 1, wherein the input-coupler and the output-coupler are positioned relative to one another to substantially achieve telecentricity.

8. The apparatus of claim 1, wherein the plurality of curved grating lines of the input-coupler are substantially concentric, each have substantially the same center of curvature that is located within the region of the waveguide at which is located the output-coupler, and each have substantially the same point of convergence that is located within the region of the waveguide at which is located the output-coupler.

9. The apparatus of claim 1, wherein the center of curvature and the point of convergence for each of the plurality of curved grating lines of the input-coupler are the same point, which is located at or near a center of the output-coupler.

10. The apparatus of claim 1, wherein an optical transfer function of the input-coupler is substantially equivalent to an optical transfer function of an on-axis holographic lens combined with an optical transfer function of a linear diffraction grating.

11. A method for use in tracking an eye, the method comprising:

illuminating an eye with infrared light while an input-coupler of a waveguide is generally axially aligned with the eye, which will result in infrared light beams reflected from the eye being incident on the input-coupler of the waveguide;

diffracting the infrared light beams that are incident on the input-coupler of the waveguide towards a common region of the waveguide at which is located an output-coupler that is spatially separated from the input-coupler, the diffracting performed using curved grating lines of the input-coupler, wherein the curved grating lines of the input-coupler each have a respective center of curvature and a respective point of convergence that are located within a region of the waveguide at which is located the output-coupler;

using the output-coupler of the waveguide, causing the infrared light beams to exit the waveguide; and causing ray bundles of the infrared light beams reflected from different field points on the eye to propagate through the waveguide at respective different angles of reflection and exit the waveguide with respective different angles of incidence relative to a surface of the waveguide through which the infrared light exits.

12. The method of claim 11, further comprising:

angularly encoding the infrared light beams that are reflected from the eye by causing ray bundles of infrared light reflected from a same field point on the eye that enter the waveguide through the input-coupler to become collimated inside of the waveguide and exit the waveguide with a same angle of incidence relative to a surface of the waveguide through which the infrared light exits.

13. The method of claim 11, further comprising:

converting the infrared light beams that exit the waveguide from angularly encoded infrared light beams to two-dimensional spatially encoded infrared light beams.

14. The method of claim 13, further comprising:

generating, in dependence on the two-dimensional spatially encoded infrared light beams, eye tracking data that can be used to track the eye; and at least one of controlling or modifying an aspect of an application based on the eye tracking data.

15. The method of claim 11, further comprising:

using the radially varying pitch of the plurality of curved grating lines of the input-coupler to cause different infrared light beams that are incident on different horizontal and vertical positions of the input-coupler to propagate through the waveguide at respective different angles of reflection and exit the waveguide at respective different angles of incidence relative to a surface of the waveguide through which the infrared light beams exit.

16. A system for use in tracking an eye, comprising:

a waveguide that is transparent and includes an input-coupler and an output-coupler that are spatially separated from one another;

an infrared illumination source that produces infrared light that can be used to illuminate an eye;

wherein the input-coupler of the waveguide comprises a plurality of curved grating lines having a radially varying pitch;

wherein the plurality of curved grating lines of the input-coupler each have a respective center of curvature and a respective point of convergence that are located within the region of the waveguide at which is located the output-coupler;

wherein when the input-coupler of the waveguide is positioned in front of an eye that is illuminated with infrared light produced by the infrared illumination source, infrared light beams reflected from the eye and incident on the input-coupler enter the waveguide at the input-coupler, propagate through the waveguide from the input-coupler to the output-coupler by way of total internal reflections, and exit the waveguide proximate the output-coupler; and wherein the radially varying pitch of the plurality of curved grating lines of the input-coupler are configured to cause different infrared light beams that are incident on different horizontal and vertical positions of the input-coupler to propagate through the waveguide at respective different angles of reflection and exit the waveguide at respective different angles of incidence relative to a surface of the waveguide through which the infrared light beams exit.

17. The system of claim 16, wherein the plurality of curved grating lines of the input-coupler are configured to:

diffract infrared light beams incident on the input-coupler into the waveguide and towards a common region at which is located the output-coupler of the waveguide; and cause the input-coupler to work as a focus element so that ray bundles of infrared light reflected from a same field point on the eye that enter the waveguide through the input-coupler become collimated inside of the waveguide and exit the waveguide with a same angle of incidence relative to a surface of the waveguide through which the infrared light exits.

18. The system of claim 16, wherein:

the radially varying pitch of the curved grating lines of the input-coupler decreases with increases in distances between the curved grating lines and the output-coupler; and for each point on each of the plurality of curved grating lines of the input-coupler the respective center of curvature is within the region of the waveguide at which is located the output-coupler.

19. The system of claim 16, further comprising:

a lens module configured to convert the infrared light beams that exit the waveguide from angularly encoded infrared light beams to two-dimensional spatially encoded infrared light beams; and a sensor configured to produce eye tracking data in dependence on the two-dimensional spatially encoded infrared light beams produced using the lens module.

20. The system of claim 19, further comprising:

a processor configured to at least one of control or modify an aspect of an application based on the eye tracking data.

* * * * *